US012738364B2

(12) United States Patent
Yerebakan et al.

(10) Patent No.: US 12,738,364 B2
(45) Date of Patent: Sep. 15, 2026

(54) METHOD FOR AUTOMATED PROCESSING OF VOLUMETRIC MEDICAL IMAGES

(71) Applicant: Siemens Healthineers AG, Forchheim (DE)

(72) Inventors: Halid Yerebakan, Carmel, IN (US); Gerardo Hermosillo Valadez, West Chester, PA (US); Yoshihisa Shinagawa, Downingtown, PA (US)

(73) Assignee: Siemens Healthineers AG, Forchheim (DE)

( * ) Notice: Subject to any disclaimer, the term of this patent is extended or adjusted under 35 U.S.C. 154(b) by 245 days.

(21) Appl. No.: 18/616,349

(22) Filed: Mar. 26, 2024

(65) Prior Publication Data

US 2024/0363230 A1 Oct. 31, 2024

(30) Foreign Application Priority Data

Apr. 26, 2023 (EP) .................................... 23170109

(51) Int. Cl.

| | |
|---|---|
| ***G16H 30/40*** | (2018.01) |
| ***G06T 7/30*** | (2017.01) |
| ***G06T 15/00*** | (2011.01) |
| ***G16H 30/20*** | (2018.01) |

(52) U.S. Cl.

CPC ............... *G16H 30/40* (2018.01); *G06T 7/30* (2017.01); *G06T 15/00* (2013.01); *G16H 30/20* (2018.01)

(58) Field of Classification Search

None

See application file for complete search history.

(56) References Cited

U.S. PATENT DOCUMENTS

| | | | | |
|---|---|---|---|---|
| 2016/0174902 | A1* | 6/2016 | Georgescu | A61B 5/7267 600/408 |
| 2017/0330319 | A1 | 11/2017 | Xu et al. | |
| 2018/0018766 | A1* | 1/2018 | Jang | G06T 7/0012 |
| 2018/0089530 | A1* | 3/2018 | Liu | G06V 10/764 |
| 2020/0327661 | A1* | 10/2020 | Oved | G16H 30/20 |
| 2021/0012514 | A1* | 1/2021 | Piat | G06V 10/7715 |
| 2021/0271914 | A1* | 9/2021 | Keshwani | G06T 7/0012 |
| 2023/0119535 | A1* | 4/2023 | Michiels | A61B 34/10 705/2 |

OTHER PUBLICATIONS

Calonder, M., Lepetit, V., Strecha, C., Fua, P. (2010). BRIEF: Binary Robust Independent Elementary Features. In: Daniilidis, K., Maragos, P., Paragios, N. (eds) Computer Vision—ECCV 2010. ECCV 2010. Lecture Notes in Computer Science, vol. 6314. Springer, Berlin, Heidelberg. https://doi.org/10.1007/978-3-642-1556.*

(Continued)

*Primary Examiner* — Henok Shiferaw

(57) ABSTRACT

A framework for automated processing of volumetric medical images. A volumetric medical image, including at least one organ or portion thereof, is received. A regression model is applied for estimating anatomical locations to a certain input, including a sub-volume of the volumetric medical image associated with a certain point of interest in the volumetric medical image or a sparse sampling descriptor associated with the certain point of interest, for outputting a normalized location or a relative location referring to a certain reference coordinate system.

20 Claims, 6 Drawing Sheets

(56) References Cited

OTHER PUBLICATIONS

A. Criminisi, D. Robertson, E. Konukoglu, J. Shotton, S. Pathak, S. White, K. Siddiqui, Regression forests for efficient anatomy detection and localization in computed tomography scans, Medical Image Analysis, vol. 17, Issue 8.*

EP search report in EP Application No. 23170109.5, dated Oct. 17, 2023, 9 pages.

* cited by examiner

METHOD FOR AUTOMATED PROCESSING OF VOLUMETRIC MEDICAL IMAGES

CROSS-REFERENCE TO RELATED APPLICATION

This application claims the benefit of priority from European Patent Application No. 23170109.5, filed on Apr. 26, 2023, the contents of which are incorporated by reference.

TECHNICAL FIELD

The present framework relates to automated processing of volumetric medical images.

BACKGROUND

Automated processes for processing volumetric medical images are essential for the automation of workflow in medical imaging. Thus, different forms of computer-implemented algorithms exist in the medical imaging industry, including registration, segmentation, landmarking, and bounding boxes. These tools inform subsequent automation algorithms about the location of interest in the human body.

A conventional way of matching the coordinates (or locations) between medical images is applying registration algorithms. Rigid registration algorithms calculate rotation and translation matrices to the images to allow mapping coordinates between coordinate systems with matrix multiplications. On the other hand, non-rigid transformations allow more flexible non-linear relationships for those mappings. In both cases, the image information should have enough overlap for accurate registration. A disadvantage of these conventional registration methods is prohibitive runtime due to a large amount of computation. These registration algorithms map all the points in the corresponding images, even only a few points may be needed to be mapped in certain applications.

Furthermore, landmarking methods may provide semantic location information in a single source image. These landmarking methods are relatively fast as compared to registration methods. However, increasing the number of landmarks increases the required amount of work for training, while decreasing the runtime speed. In other words, there is an inherent tradeoff between the granularity of landmarks and speed.

SUMMARY

Described herein is a framework for automated processing of volumetric medical images. A volumetric medical image, including at least one organ or portion thereof, is received. A regression model is applied for estimating anatomical locations to a certain input, including a sub-volume of the volumetric medical image associated with a certain point of interest in the volumetric medical image or a sparse sampling descriptor associated with the certain point of interest, for outputting a normalized location or a relative location referring to a certain reference coordinate system.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
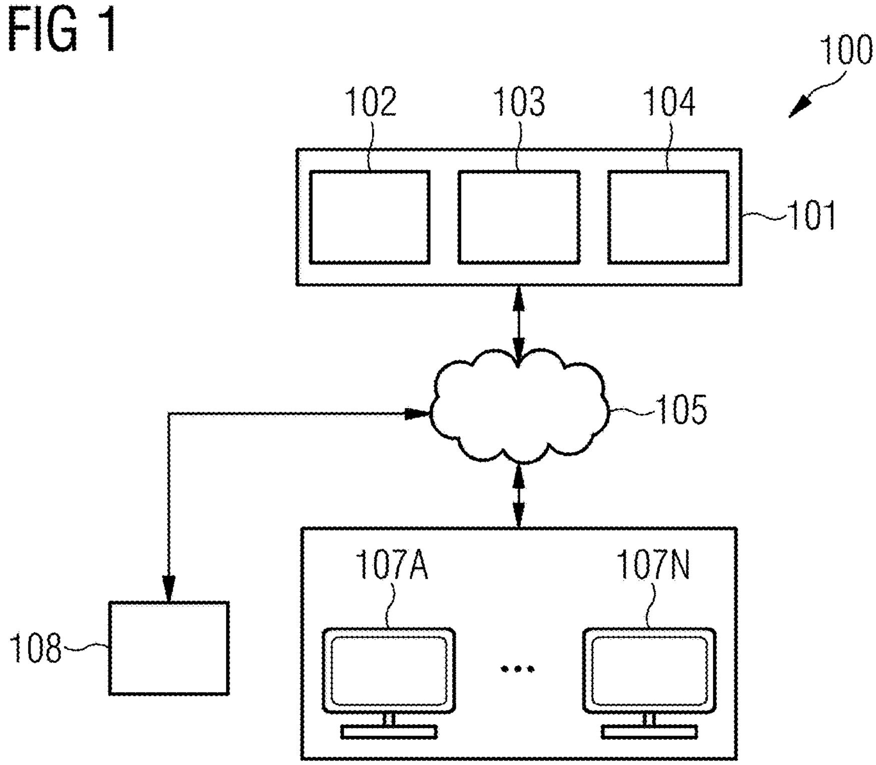
FIG. 1 illustrates a block diagram of a client-server architecture embodying a system for automated processing of volumetric medical images.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance. Independent of the grammatical term usage, individuals with male, female or other gender identities are included within the term."

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

According to a first aspect, a computer-implemented method for automated processing of volumetric medical images is provided. The method comprises: a) receiving a volumetric medical image, the volumetric medical image comprising at least one organ or portion thereof, and b) applying a regression model for estimating anatomical locations to a certain input, the certain input including a sub volume of the volumetric medical image associated with a certain point of interest in the volumetric medical image or a sparse sampling descriptor associated with the certain point of interest, for outputting a normalized location or a relative location referring to a certain reference coordinate system.

By using a regression model for estimating anatomical locations, anatomical location normalization is improved. In the present method, increasing image size, in particular beyond the trajectory path, advantageously does not increase the running time due to the use of the regression model. As input to the regression model, a certain sub-volume of the volumetric medical images or a number of sparse sampling descriptors associated with a certain point of interest in the volumetric medical image may be used. In other words, as input for the regression model, the raw image data or any pre-transformation of the volumetric medical image or sparse sampling descriptors may be used. Using sparse sampling descriptors as input has the advantage of low computational overhead. Hence, in many applications, it operates faster. In this regard, low computational overhead may allow running the present method for multiple locations, which in turn may improve the precision of the location estimation.

The volumetric medical image may be captured by and received from a medical imaging unit, the medical imaging unit may include, for example, but not limited to, a magnetic resonance imaging device, a computer tomography device, an X-ray imaging device, an ultrasound imaging device, etc. The volumetric medical image may be three-dimensional (3D) and/or related to a volume. The volumetric medical image may be made up of a number of slices, i.e., 2D (two-dimensional) medical images. The 2D medical images may be captured by and received from the medical imaging unit mentioned above. The 2D medical images may then be assembled to form the volumetric medical image.

An organ is to be understood as a collection of tissue joined in a structural unit to serve a common function. The organ may be a human organ. The organ may be any one of the following, for example: intestines, skeleton, kidneys, gall bladder, liver, muscles, arteries, heart, larynx, pharynx, brain, lymph nodes, lungs, spleen bone marrow, stomach, veins, pancreas, and bladder.

In one embodiment, the regression model includes a trained neural network. Particularly, the neural network is trained to embody a normalized coordinate estimator for point matching between locations in the volumetric medical image and locations in the certain reference coordinate system. The present normalized coordinate estimator may use raw image data or sparse sampling descriptors as input. Sparse sampling descriptors (also referred to as point matching descriptors) further provide additional speed gains thanks to a lower dimension. The output of the normalized coordinate estimator is the normalized coordinates between 0 and 1, where (0,0,0) is the bottom right anterior corner of the atlas and (1,1,1) is the top left posterior corner, for example.

In a further embodiment, the method further comprises receiving a command, in particular a user input, for determining the certain point of interest. Thus, the point of interest may be selected by a user. For example, the point of interest can be selected using a graphical user interface and an input device, such as a pointer device, to interact with the graphical user interface to select the point of interest. In another embodiment, the point of interest may be input using a keyboard, a data file or the like. According to a further embodiment, the point of interest is selected by pausing a cursor operated by the user on the volumetric medical image or a part thereof displayed on the graphical user interface. "Pausing" here means that the cursor is not moved by the operator. This allows for a quick and efficient analysis of a volumetric medical image by a user, for example a doctor.

In a further embodiment, the method further comprises: providing a sparse sampling model for sparse sampling the volumetric medical image, the sparse sampling model defining a number N of sampling points distributed in the volumetric medical image and defining locations and distances of the distributed sampling points, wherein the sparse sampling model is particularly provided in dependence on the received command, and sampling voxels from the volumetric medical image using the provided sparse sampling model for obtaining sparse sampling descriptors.

Presently, a voxel represents a value in three-dimensional space, whereas a pixel represents a value in two-dimensional space. The pixels or voxels may or may not have their position, i.e., their coordinates explicitly encoded with their values. Instead, the position of a pixel or voxel is inferred based upon its position relative to other pixels or voxels (i.e., is positioned in the data structure that makes up a single 2D or 3D (volumetric) image). The voxels may be arranged on a 3D grid, the pixels on a 2D grid. The 2D medical image may, for example, be in the form of an array of pixels. The volumetric medical image may comprise an array of voxels. The pixels of a number of 2D medical images making up a volumetric medical image are also presently referred to as voxels. The pixels or voxels may be representative of intensity, absorption or other parameters as a function of a three-dimensional position, and may, for example, be obtained by a suitable processing of measurement signals obtained by one or more of the above-mentioned medical imaging units.

"Sparse sampling" is to be understood as, with regard to the total number of voxels making up the volumetric medical image, only few voxels being used in sampling. In particular, "sparse" is to say that less than 50% or less than 20% or even less than 10% of the total number of voxels of the volumetric medical image are sampled in step c). Sparse sampling has the effect that the amount of data which needs to be processed by the trained classifier is reduced, thus reducing computation time and computation resources. Even though the amount of data processed by the trained classifier is reduced, the inventors found that location estimation can still be provided in good quality, and a type of organ can particularly be identified reliably using the present approach. One reason for this is that the sampled voxels may correspond to a larger field of view, thus also considering neighborhood information, compared to the case where every voxel of a smaller sub volume is sampled. The sampling model particularly contains the information about the location of the voxels in the volumetric medical image which are to be sampled, i.e., the sampling points distributed in the volumetric medical image and the locations and distances of the distributed sampling points. The sampling model can be or make use of an algorithm, for example.

The sparse sampling model is particularly provided such that the voxels are sampled with a sampling rate per unit length, area or volume which decreases with a distance of the respective voxel on the certain point of interest.

In particular, the sampling rate decreases at a non-linear rate, in particular at the rate of an exponential logarithmic or a power function. The inventors found that using a sampling rate as described reduces computation time significantly, while, at the same time, providing location estimations reliably. In particular, the sampled voxels are less than 1%, preferably less than 0.1%, and more preferably less than 0.01% of the total number of voxels in the volumetric medical image.

In a further embodiment, the sparse sampling model defines a plurality of grids, in particular 3D grids, of different grid spacings, the different grid spacings determining different distances of the distributed sampling points in the volumetric medical image. The respective grid spacing is defined as the distance between two adjacent nodes of the respective grid, wherein the respective node is defined as the intersection of three grid lines and forms a sampling point.

The respective sparse sampling descriptor may be formed as a vector of values, in particular, of intensities, of the sampled voxels associated with a certain sampling point of the distributed sampling points.

In a further embodiment, the certain reference coordinate system is an atlas having a plurality of coordinates. Particularly, the atlas includes a single reference volume of the at least one organ or the portion thereof.

In a further embodiment, in the atlas, at least one coordinate of the plurality of coordinates of the atlas is associated with injected knowledge. Particularly, said injected knowledge includes semantic anatomical information.

In a further embodiment, the step b) is embodied by: applying a regression model for estimating anatomical locations to a certain input, the certain input including a sub-volume of the volumetric medical image associated with a certain point of interest in the volumetric medical image or a sparse sampling descriptor associated with the certain point of interest, for outputting a normalized location referring to the atlas. The present embodiment provides a normalized atlas coordinate estimation, including mapping source point to atlas.

For example, the certain reference coordinate system is an atlas. An atlas is a single reference volume. Annotating a single atlas image is simpler as compared to machine learning dataset curation for each anatomical landmark since it is a one-time effort. Thus, locations of points or coordinates on the atlas image may be associated with semantic anatomical information easily. Estimating the mapping of any point in the source image, i.e., the received volumetric medical image, to the atlas image, will associate the information with the point of interest in the source image.

For example, if the question is "what is the organ for the selected point", the segmentation mask of the atlas image may instantly provide the organ label from atlas image segmentation once mapping to atlas is complete. Another example is if the question is "how far is the point of interest from a specific landmark location", the desired landmark location in the atlas image may be checked and mapped back to the image of interest.

For the present embodiment of normalized atlas coordinate estimation, a machine learning regression model, in particular a residual network, may be used as the trained neural network embodying or applying the regression model. For providing the normalized locations, the residual network may include multiple layers. A first layer may be a dimension reduction layer receiving the sparse sampling descriptors as input. Further layers of the residual network include linear projection, normalizing, activation, linear projection and normalization. Finally, a three-dimensional sigmoid function squeezes output to 0-1 range for the normalized X, Y, Z locations or coordinates.

A challenge of training the present embodiment of normalized atlas coordinate estimation is establishing ground truth for normalized coordinates. As manual annotation of mapping points is both unnecessary and tedious, an automated registration algorithm may be used to create a mapping of input images to atlas coordinates. Presently, this low speed of non-rigid registrations does not matter here, since it is a one-time effort for training time. Once the mapping is obtained in training data, coordinates are normalized between 0-1 by dividing the voxel location to the atlas volume size. This normalization improves neural network training. In sum, the computational burden is switched from runtime to training.

In the runtime, the trained model (or neural network) gets the input from the selected point and estimates the normalized coordinate. This normalized coordinate may be mapped back to the atlas voxel location by multiplying by the atlas volume size. This single point estimation may establish the mapping between the source volume and the atlas volume. However, multiple points nearby may be taken into account to improve robustness.

In a further embodiment, the method further comprises: mapping the certain point of interest of the volumetric medical image to a certain normalized location of the atlas and associating knowledge around that certain normalized location from the atlas.

In a further embodiment, the method further comprises: mapping the certain point of interest of the volumetric medical image to the atlas, wherein the mapping includes allocating the injected knowledge being associated with the coordinate of the atlas being mapped to the certain point of interest to the certain point of interest.

Thus, the knowledge injected to the atlas may be mapped to the corresponding point in the volumetric medical image. Therefore, injected knowledge may be used for the received medical image.

In a further embodiment, the certain reference coordinate system uses at least a certain landmark in the volumetric medical image, wherein the step b) is embodied by applying a regression model for estimating anatomical locations to a certain input, the certain input including a sparse sampling descriptor associated with the certain point of interest, for outputting a relative location referring to the certain landmark. In particular, for a certain location, the sparse sampling descriptor associated with the certain location is provided and a displacement from the certain landmark is determined, in particular estimated.

The present embodiment provides landmark displacement estimation (source point to landmark). In the present embodiment, the coordinates (or locations) are normalized by taking the landmark of the source image, i.e., the received volumetric medical image, as the origin and the displacement from the origin is estimated for a given point. In this embodiment, there may be no atlas involved. For a given starting location, the present embodiment extracts the sparse sampling descriptor for that location and estimates the displacement from the landmark.

The training steps may be similar to the previous embodiment of normalized atlas coordinate estimation. However, there may be two differences. First, the ground truth generation for a point may be done by detecting the landmark, such as "Carina tracheae", and subtracting coordinates to compute displacement vectors. Second, since there is no normalization in the displacement, the last layer of the neural network is linear instead of the sigmoid (which is 0-1 range).

However, navigating to landmarks may be direct, and mapping to atlas may be indirect. For example, for a selected path, the regression model may estimate the displacement and then subtract this displacement from the current location to estimate the landmark location. Similarly, if one would like to associate the atlas level information, the selected landmark may be used as the origin in the atlas to map coordinates from the source volume to the atlas volume.

Since single step displacement estimation may be a rough estimate, it may be possible to further refine the estimation after moving to first estimation. A nearby location to the desired landmark may perform better in many applications. Even in multiple iterations, the present embodiment is much more efficient than doing an exhaustive search for landmark location estimation.

In a further embodiment, the step b) is embodied by: applying a conditional regression model for estimating anatomical locations to a certain input, the certain input including a first sparse sampling descriptor associated with the certain point of interest in the volumetric medical image and a second sparse sampling descriptor associated with a certain target location in the atlas, for outputting a relative displacement vector referring to the atlas. The present embodiment provides conditional estimation (mapping atlas point to source).

The above discussed embodiment of landmark displacement estimation only gives the output for a fixed number of landmarks. Thus, only a limited number of landmarks may be trained due to the needs for annotations required for training them. Instead, in the present embodiment of conditional estimation, the used conditional regression model may find any anatomical atlas location in the query image. The present embodiment of conditional estimation may also associate the atlas information to the source volume. Landmarks may be a special case of the present embodiment of conditional estimation which are the annotated places in the atlas. Adding new landmarks may be reduced to a single point selection on the atlas image.

To provide relative displacement regarding the atlas location, the present output depends on both the source and selected atlas location in the conditional regression model. Thus, the conditional regression model uses two descriptors, namely the above-mentioned first sparse sampling descriptor and the above-mentioned second sparse sampling descriptor. Both sparse sampling descriptors are combined into neural network input and the neural network embodying the conditional regression model estimates the relative displacement vector.

In particular, for a specific runtime application, the whole atlas is not necessary advantageously. For example, if one would like to find the middle of the lung, only the specific atlas descriptor is provided in the application. Additionally, multiple descriptors may be given to obtain multiple locations for robustness.

The training step for the present embodiment of conditional estimation involves ground truth generation as in the previous described embodiments. The output for the present embodiment is relative displacement between any two locations. This pair of locations may be sampled from source image and atlas after the registration of images to compute displacement. Also, they may be obtained purely from only the source image by utilizing existing a world coordinate frame. The later ground truth generation method further removes the need of using registration methods.

In a further embodiment, the method further comprises: storing findings in the volumetric medical image using the output normalized location or the output relative location.

In particular, a robot, (e.g., CT or MR) scanner or other device or machine is controlled depending on the stored findings. The robot may be configured for operating on a patient's body, for example. In particular, a robot (e.g., an operating instrument thereof such as a scalpel) or scanner movement may be controlled depending on the stored findings.

In a further embodiment, the method further comprises: determining, based on the output normalized location or the output relative location, all the information associated with the certain point of interest and/or associated with at least a location nearby the certain point of interest.

In a further embodiment, the method further comprises: executing image registration based on the output normalized location or the output relative location, particularly including matching the certain point of interest to a location in a further image, in particular in a further volumetric medical image.

According to a second aspect, a computer-implemented device for automated processing of volumetric medical images is provided, the computer-implemented device comprising: one or more processing units, a receiving unit which is configured to receive one or more volumetric medical images captured by a medical imaging unit, and a non-transitory memory coupled to the one or more processing units, the non-transitory memory comprising a module configured to perform the method steps of the first aspect or of any embodiment of the first aspect.

The respective unit, e.g., the processing unit or the receiving unit, may be implemented in hardware and/or in software. If said unit is implemented in hardware, it may be embodied as a device, e.g., as a computer or as a processor or as a part of a system, e.g., a computer system. If said unit is implemented in software, it may be embodied as a computer program product, as a function, as a routine, as a program code or as an executable object.

The embodiments and features according to the first aspect are also embodiments of the second aspect.

According to a third aspect, a system for automated processing of volumetric medical images is provided, the system comprising: one or more servers, a medical imaging unit coupled to the one or more servers, the one or more servers, comprising instructions, which when executed causes the one or more servers to perform the method steps of the first aspect or of any embodiment of the first aspect.

The embodiments and features according to the first aspect are also embodiments of the third aspect.

According to a fourth aspect, a computer program product is provided, the computer program product comprising machine readable instructions, that when executed by one or more processing units, cause the one or more processing units to perform the method steps of the first aspect or of any embodiment of the first aspect.

The embodiments and features according to the first aspect are also embodiments of the fourth aspect.

A computer program product, such as a computer program means, may be embodied as a memory card, USB stick, CD-ROM, DVD or as a file which may be downloaded from a server in a network. For example, such a file may be provided by transferring the file comprising the computer program product from a wireless communication network.

According to a fifth aspect, one or more non-transitory computer readable media on which program code sections of a computer program are saved, the program code sections being loadable into and/or executable in a system to make the system execute the method steps of the first aspect or of any embodiment of the first aspect when the program code sections are executed in the system.

The embodiments and features according to the first aspect are also embodiments of the fifth aspect.

The realization by a computer program product and/or a computer-readable medium has the advantage that already existing management systems can be easily adopted by software updates in order to work as proposed by the framework.

"A" is to be understood as non-limiting to a single element. Rather, one or more elements may be provided, if not explicitly stated otherwise. Further, "a", "b" etc. in steps a), step b) etc. is not defining a specific order. Rather, the steps may be interchanged as deemed fit by the skilled person.

Further possible implementations or alternative solutions of the framework also encompass combinations—that are not explicitly mentioned herein—of features described above or below with regard to the embodiments. The person skilled in the art may also add individual or isolated aspects and features to the most basic form of the framework.

Hereinafter, embodiments for carrying out the present framework are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

FIG. 1 provides an illustration of a block diagram of a client-server architecture embodying a system for automated processing of volumetric medical images MI (see FIG. 4) The client-server architecture 100 comprises a server 101 and a plurality of client devices 107A-N. Each of the client devices 107A-N is connected to the server 101 via a network 105, for example, local area network (LAN), wide area network (WAN), WIFI, etc. In one embodiment, the server 101 is deployed in a cloud computing environment. As used herein, "cloud computing environment" refers to a processing environment comprising configurable computing physical and logical resources, for example, networks, servers, storage, applications, services, etc., and data distributed over the network 105, for example, the internet. The cloud computing environment provides on-demand network access to a shared pool of the configurable computing physical and logical resources. The server 101 may include a medical database 102 that comprises medical images related to a plurality of patients that is maintained by a healthcare service provider. In an embodiment, the medical database 102 comprises volumetric medical images captured by a MR scanner and/or by a CT scanner. The server 101 may include a module 103 that is configured to perform identifying a type of organ in a volumetric medical image, in particular as described hereinafter.

The client devices 107A-N are user devices, used by users, for example, medical personnel such as a radiologist, pathologist, physician, etc. In an embodiment, the user device 107A-N may be used by the user to receive volumetric medical images or 2D medical images associated with the patient. The data can be accessed by the user via a graphical user interface of an end user web application on the user device 107A-N. In another embodiment, a request may be sent to the server 101 to access the medical images associated with the patient via the network 105.

An imaging unit 108 may be connected to the server 101 through the network 105. The unit 108 may be a medical imaging unit 108 capable of acquiring a plurality of volumetric medical images. The medical imaging unit 108 may be, for example, a scanner unit such as a magnetic resonance imaging unit, computed tomography imaging unit, an X-ray fluoroscopy imaging unit, an ultrasound imaging unit, etc.

Figure 2:
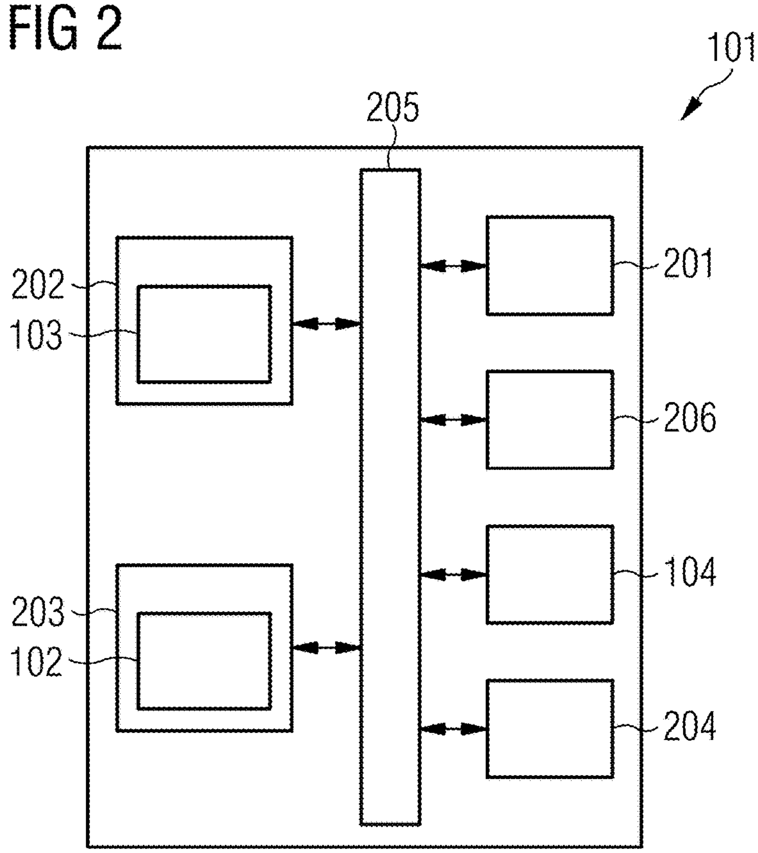
FIG. 2 illustrates a block diagram of a data processing system embodying a device for automated processing of volumetric medical images.

FIG. 2 is a block diagram of a data processing system 101 in which an embodiment can be implemented, for example, as a system 101 for automated processing of volumetric medical images MI, configured to perform the processes as described herein. It is appreciated that the server 101 is an exemplary implementation of the system in FIG. 2. In FIG. 2, said data processing system 101 comprises a processing unit 201, a memory 202, a storage unit 203, an input unit 204, an output unit 206, a bus 205, and a network interface 104.

The processing unit 201, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 101 may also include embedded controllers, such as generic or programmable logic devices or arrays, application specific integrated circuits, single-chip computers, and the like.

The memory 202 may be one or more non-transitory media, such as volatile memory and non-volatile memory. The memory 202 may be coupled for communication with said processing unit 201. The processing unit 201 may execute instructions and/or code stored in the memory 202. A variety of computer-readable storage media may be stored in and accessed from said memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 201 comprises a module 103 stored in the form of machine-readable instructions on any of said above-mentioned storage media and may be in communication to and executed by processing unit 201. When executed by the processing unit 201, the module 103 causes the processing unit 201 to provide location estimate. Method steps executed by the processing unit 201 to achieve the abovementioned functionality are elaborated upon in detail in the following figures.

The storage unit 203 may be one or more non-transitory storage media which store the medical database 102. The input unit 204 may include input means such as keypad, touch-sensitive display, camera (such as a camera receiving gesture-based inputs), a port etc. capable of providing input signal such as a mouse input signal or a camera input signal. The bus 205 acts as interconnect between the processor 201, the memory 202, the storage unit 203, the input unit 204, the output unit 206 and the network interface 104. The volumetric medical images may be read into the medical database 102 via the network interface 104 or the input unit 204, for example.

Those of ordinary skilled in the art will appreciate that said hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter also may be used in addition or in place of the hardware depicted. Said depicted example is provided for the purpose of explanation only and is not meant to imply architectural limitations with respect to the present disclosure.

A data processing system 101 in accordance with an embodiment of the present disclosure may comprise an operating system employing a graphical user interface (GUI). Said operating system permits multiple display windows to be presented in the graphical user interface simultaneously with each display window providing an interface to a different application or to a different instance of the same application. A cursor in said graphical user interface may be manipulated by a user through a pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Washington may be employed if suitably modified. Said operating system is modified or created in accordance with the present disclosure as described. Disclosed embodiments provide systems and methods for processing medical images.

Figure 3:
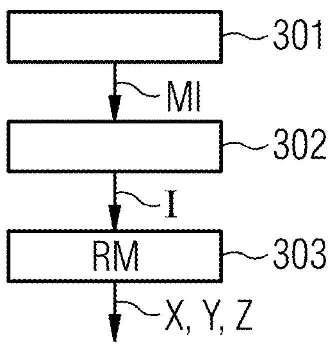
FIG. 3 illustrates a flowchart of a first embodiment of a computer-implemented method for automated processing of volumetric medical images.

FIG. 3 illustrates a flowchart of an embodiment of a method for automated processing of volumetric medical images MI. The method of FIG. 3 is discussed with reference to FIG. 4 and FIG. 5. The method of FIG. 3 includes the method steps 301-303.

Figure 4:
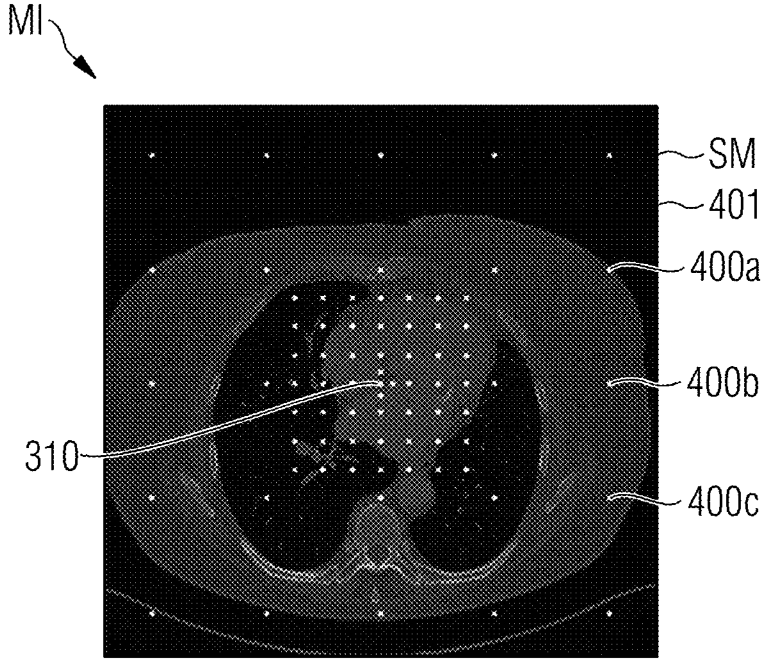
FIG. 4 illustrates a slice from a volumetric medical image and including portions of a sparse sampling model according to an embodiment.

In step 301, a volumetric medical image MI (see FIG. 4 and FIG. 5) is received. In this regard, FIG. 4 shows a 2D slice 401 taken from a volumetric medical image MI and FIG. 5 shows an example of a volumetric medical image MI.

Figure 5:
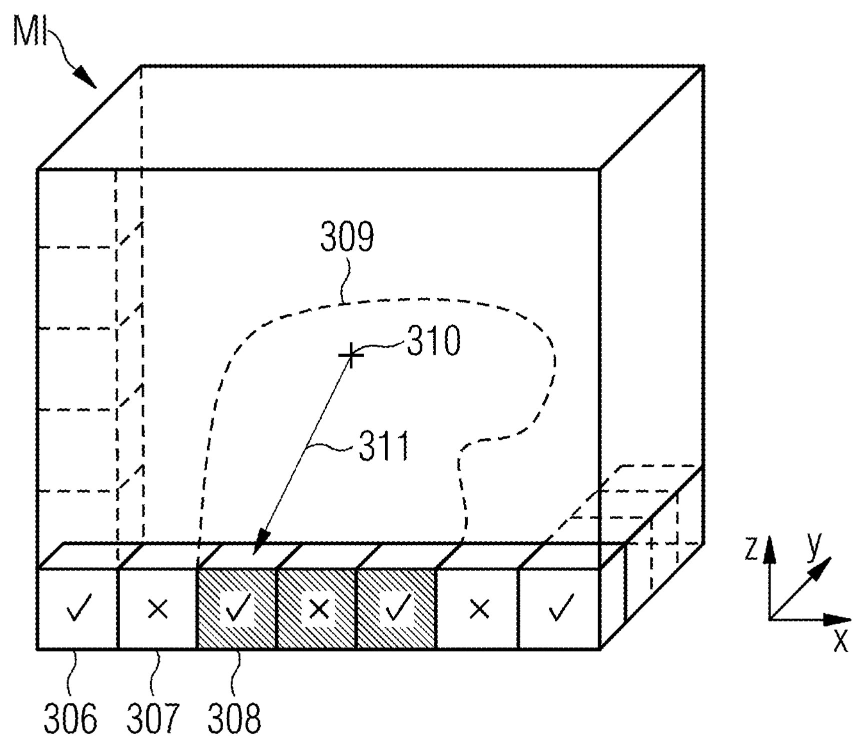
FIG. 5 shows an example of a volumetric medical image with some voxels being scanned, others being skipped.

The volumetric medical image MI as shown in FIG. 5 is comprised of a three-dimensional array of voxels 306, 307, 308. This array is illustrated in FIG. 5 as a cuboid seen in a perspective view. The cuboid comprises rows and columns of voxels 306, 307, 308 extending in all three dimensions x, y, z. To make FIG. 5 more readable, only some of the voxels 306, 307, 308 within the cuboid are shown.

Instead of the three-dimensional array, the method explained herein may also use a number of slices (two-dimensional arrays of pixels) which, taken together, describe a (three-dimensional) volume. In fact, any other data structure may be used comprising values, such as intensities, and describing a three-dimensional space. Any such value is termed a "voxel" herein. The value may be combined with information describing its three-dimensional relationship with respect to other values, or the three-dimensional relationship can be inferred from the data structure, or any other source.

The volumetric medical image MI comprises at least one organ 309 or a portion thereof. In the example of FIG. 5, a portion of an organ 309, for example lungs or kidney, is represented by hashed voxels 308 in the volumetric medical image MI.

In FIG. 5, a point of interest 310 within the volumetric medical image MI is illustrated. As explained above, the point of interest 310 may be selected by a user, for example, through a graphical user interface using a pointer device, such as a mouse. The point of interest 310 may be received, for example, through the network interface 104 or the input unit 204 (see FIG. 2).

The point of interest 310 is a point in the volumetric medical image MI for which it may be desired to identify the type of organ 309 corresponding to said point, for example. The point of interest 310 may be described through coordinates in x, y, z and may correspond to a specific voxel in the cuboid. If, for example, a mouse is used to select the point of interest 310, the coordinates of the mouse cursor, once the selection of the single point of interest 310 is done, for example by clicking or pausing the cursor over the image, said coordinates x, y, z are transmitted, for example, via the input unit 204 to the data processing system 101.

In step 302, a certain input I for a regression model RM for estimating anatomical locations is provided. The certain input I particularly includes a sub-volume of the volumetric medical image MI associated with a certain point of interest 310 (see FIG. 4 and FIG. 5) in the volumetric medical image MI or a sparse sampling descriptor D (see FIG. 6, for example) associated with the certain point of interest 310.

For the case that a number of sparse sampling descriptors D are used for the certain input I, the step 302 may include the following sub steps: (1) providing a sparse sampling model SM (see FIG. 4) for sparse sampling the volumetric medical image MI, the sparse sampling model SM defining a number of sampling points 400*a*-400*c* distributed in the volumetric medical image MI and defining locations and distances of the distributed sampling points 400*a*-400*c*, wherein the sparse sampling model SM is particularly provided in dependence on a received command, and (2) sampling voxels 306-308 (see FIG. 5) from the volumetric medical image MI using the provided sparse sampling model SM for obtaining sparse sampling descriptors D (see FIG. 6, for example).

In particular, the sparse sampling model SM is provided such that the voxels 306-308 are sampled with a sampling rate per unit length, area or volume which decreases with a distance 311 (see FIG. 5) of the respective voxel 306-308 on the point of interest 310. According to the sparse sampling model SM, at least one voxel 307 is skipped between two voxels 306, 308 that are to be sampled. In FIG. 5, the voxels that are to be sampled are designated with a tick, whereas voxels that are skipped or not sampled are designated with a cross. In the embodiment of FIG. 5, in the row of voxels defined by adjacent voxels 306, 307, 308 only every second voxel 306, 308 is sampled. The voxels 306, 308 may be sampled sequentially or in parallel.

In particular, the inventors found that it is beneficial if the voxels 306, 308 that are to be sampled are sampled with a sampling rate per unit length, area or volume which decreases with a distance 311 from the point of interest 310. It was found that results improve even more, when the sampling rate decreases at a nonlinear rate, in particular at the rate of an exponential, logarithmic or power function.

In this regard, it is referred to FIG. 4 which shows an example of a sparse sampling model SM (only some of the sampling points of the sampling model SM have been marked with reference numerals 400*a*, 400*b*, 400*c* for reasons of readability of FIG. 4) in a 2D slice 401 taken from a volumetric medical image MI. The sampling model SM is designed to provide for a sparse sampling with a sampling rate per unit volume which decreases with a distance in the x-, y- and z-direction. Since FIG. 4 shows a 2D image, the y-direction which corresponds to the depth normal to the plane of the image shown in FIG. 4 is not illustrated but corresponds to the sampling rate shown for the directions x and z in FIG. 4.

The voxels 306, 308 (see FIG. 5) from the volumetric medical image MI are sampled using the provided sparse sampling model SM for obtaining sparse sampling descriptors D. The respective sparse sampling descriptor D may be formed as a vector of values, in particular of intensities, of the sampled voxels associated with a certain sampling point 400*a*-400*c* of the distributed sampling points 400*a*-400*c*.

In step 303, a regression model RM for estimating anatomical locations is applied to the certain input I for outputting a normalized location X, Y, Z or a relative location Δx, Δy, Δz referring to a certain reference coordinate system A, L. For example, the certain reference coordinate system A, L is embodied by an atlas A. The atlas A may have a plurality of coordinates, wherein said atlas A includes a single reference volume of the at least one organ 309 or the portion thereof.

For example, the regression model RM includes a trained neural network. The neural network is particularly trained to embody a normalized coordinate estimator for point matching between locations in the volumetric medical image MI and locations in the certain reference coordinate system A, L.

Figure 6:
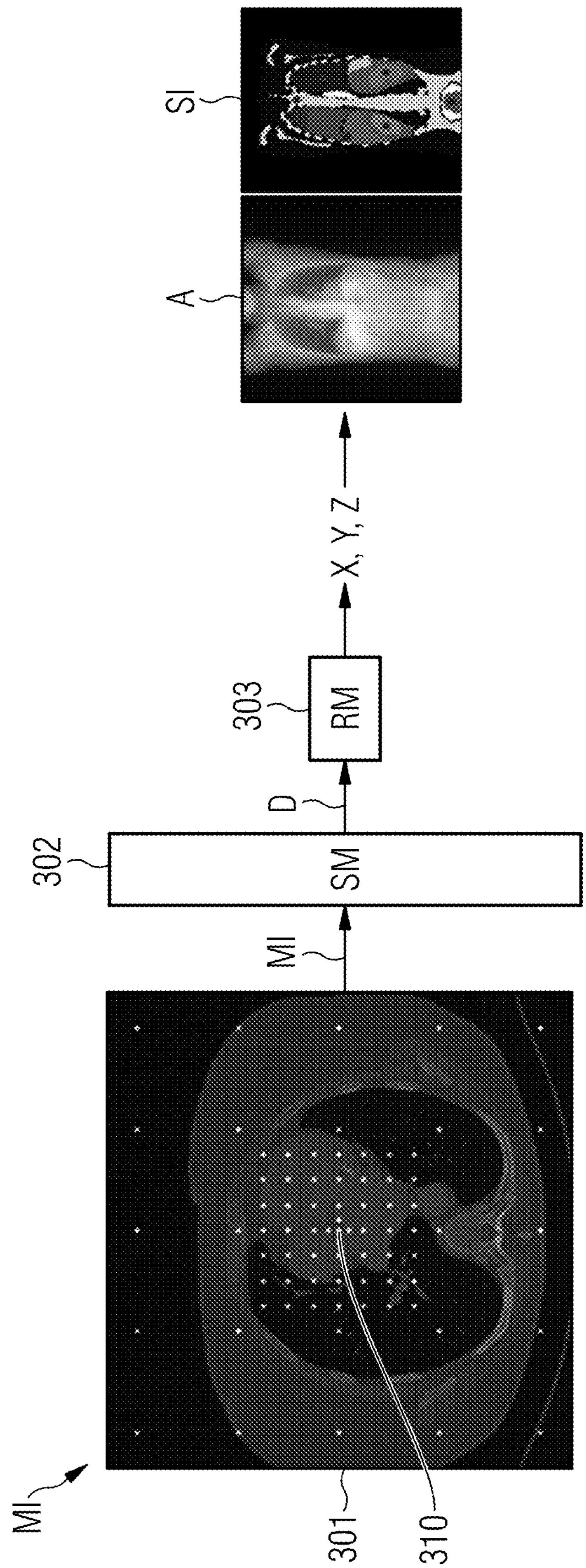
FIG. 6 illustrates a flowchart of a second embodiment of a computer-implemented method for automated processing of volumetric medical images.

Moreover, FIG. 6 shows a flowchart of a second embodiment of a computer-implemented method for automated processing of volumetric medical images MI. The method of FIG. 6 is based on the first embodiment of FIG. 3 and includes all its features. Further, in the second embodiment of FIG. 6, the certain reference coordinate system is an atlas A as shown in the right part of said FIG. 6. In the atlas A, at least one coordinate of the plurality of coordinates of the atlas A may be associated with injected knowledge. For example, the injected knowledge includes a semantic anatomical information.

As the first embodiment of FIG. 3, the second embodiment of FIG. 6 comprises the method steps 301-303. In step 301, a volumetric medical image MI is received, the volumetric medical image MI comprising at least one organ 309 or a portion thereof.

In step 302, a certain input I corresponding to a sparse sampling descriptor D is provided. Details for providing a number of sparse sampling descriptors D based on a received volumetric medical image MI are described above. In step 303, a regression model RM is applied to the sparse sampling descriptor D associated with a certain point of interest 310 such that a normalized location X, Y, Z referring to the atlas A is output. By means of the normalized location(s) X, Y, Z, structured information SI as shown in the right part of FIG. 3 may be provided. Said right part of FIG. 3 shows the atlas A and the corresponding structured information SI.

The second embodiment of the present method according to FIG. 6 may include a step of mapping the certain point of interest 310 of the volumetric medical image MI to a certain normalized location X, Y, Z of the atlas A and a step of associating knowledge around that certain normalized location from the atlas A.

Figure 7:
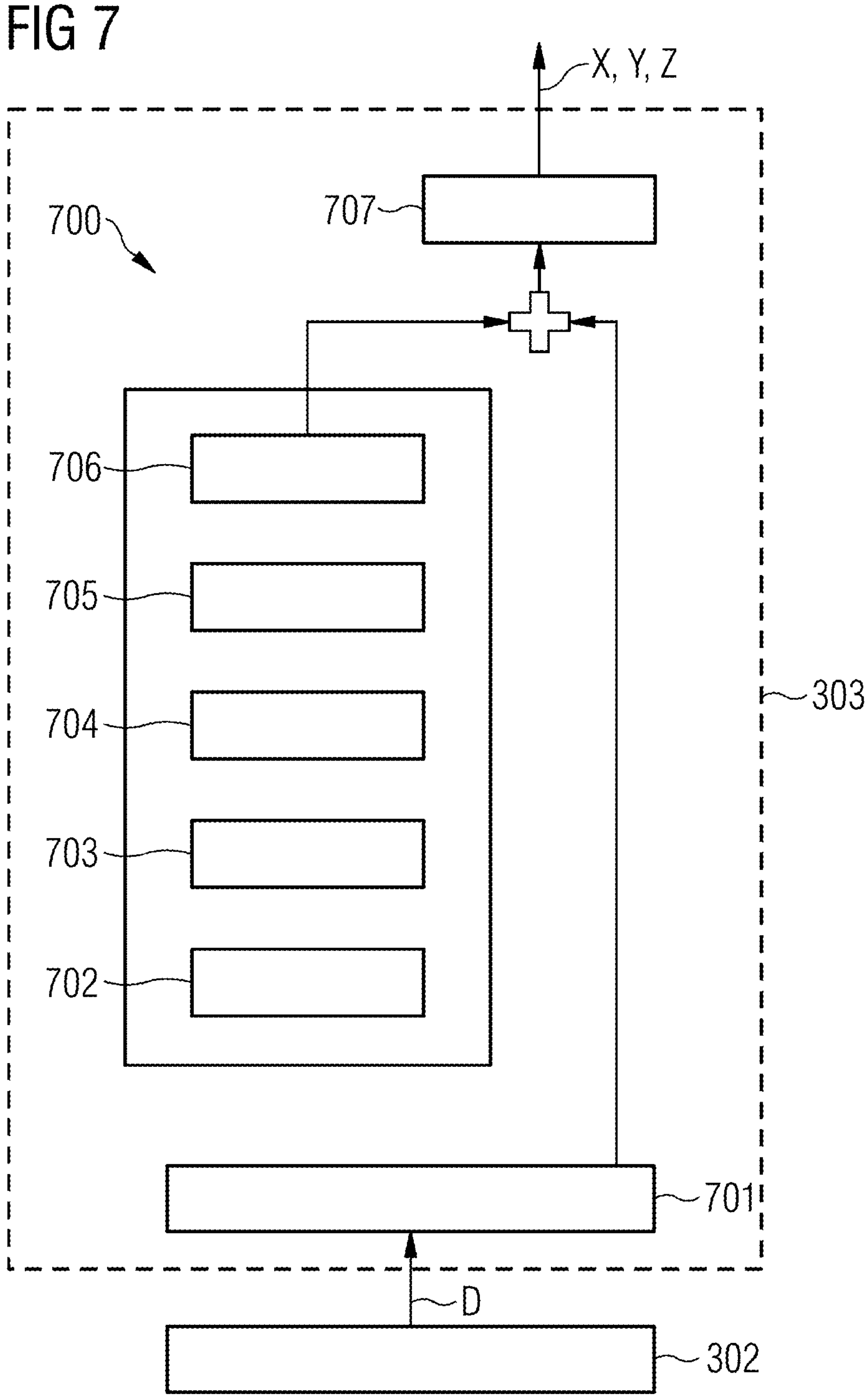
FIG. 7 illustrates a flowchart of an embodiment of the providing step and the applying step of the computer-implemented method of FIG. 6.

As indicated above, the regression model RM may include a trained neural network. The trained neural network may be a machine learning regression 700, in particular a residual network model. For example, a residual network 700 as shown in FIG. 7 may be used. In detail, FIG. 7 is a flowchart of an embodiment of the providing step 302 and the applying step 303 of the computer-implemented method of FIG. 6. As discussed with reference to FIG. 6, the providing step 302 outputs sparse sampling descriptors D. Further, as shown in FIG. 6, as well as in FIG. 7, the applying step 302 receives the sparse sampling descriptors. D. The applying step 303 has as outputs the normalized locations X, Y, Z. For providing the normalized locations X, Y, Z, the residual network 700 is used. At first, the residual network 700 gets the sparse sampling descriptor D and projects it into lower dimensional space by layer 701. Then, it applies a number of layers of residual blocks including linear projection 702, normalization 703, activation 704, linear projection 705, and normalization 706. Finally, a three-dimensional sigmoid function 707 squeezes output to 0-1 range for the normalized X, Y, Z locations or coordinates.

Figure 8:
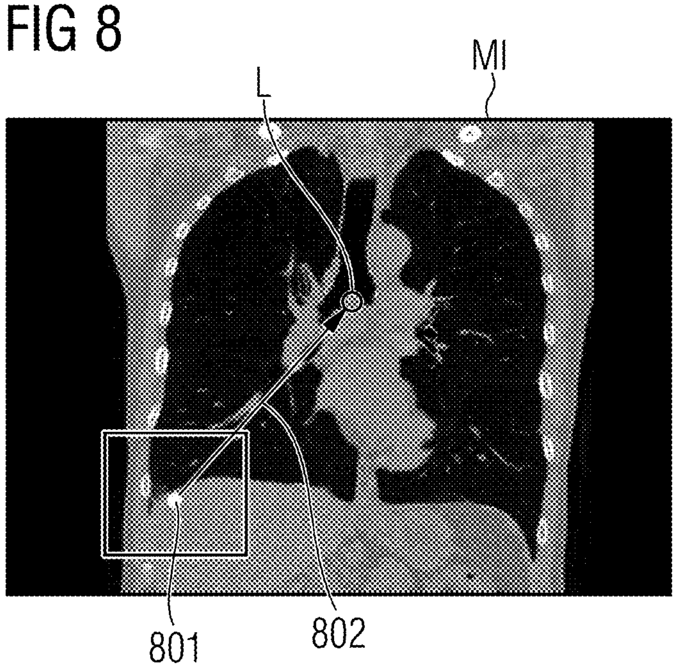
FIG. 8 illustrates an embodiment of landmark displacement estimation.

Furthermore, FIG. 8 illustrates an embodiment of landmark displacement estimation as an example for a computer-implemented method for automated processing of volumetric medical images MI. The method of FIG. 8 is based on the first embodiment of FIG. 3 and includes all its features.

In the example of FIG. 8, the certain reference coordinate system A, L uses at least a certain landmark L in the volumetric medical image MI. As FIG. 8 shows, the certain landmark L is "Carina tracheae" as indicated by the small circle. According to the embodiment of FIG. 8, step 303 is embodied by applying a regression model RM for estimating anatomical locations to a sparse sampling descriptor D associated with a certain point of interest 310, 801 for outputting a relative location referring to the certain landmark L. In this method, there is no atlas A involved. For example, for the giving starting location 801, the method extracts the descriptor D for that location and estimates the displacement 802 from the landmark L, for example "Carina tracheae" as shown in FIG. 8.

Figure 9:
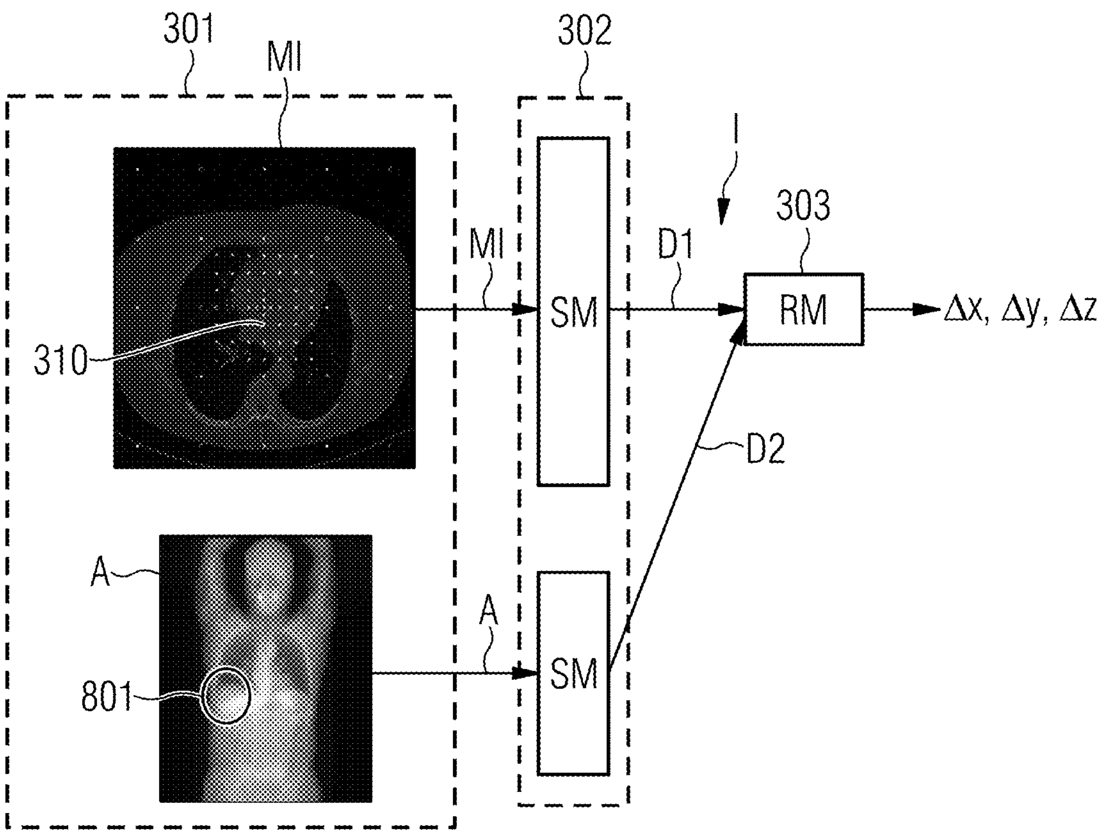
FIG. 9 illustrates a flowchart of a third embodiment of a computer-implemented method for automated processing of volumetric medical images.

Further, FIG. 9 shows a flowchart of a third embodiment of a computer-implemented method for automated processing of volumetric medical images MI.

As the methods of FIGS. 3 and 6, the method of FIG. 9 comprises embodiments of method steps 301-303.

In step 301 of FIG. 9, a volumetric medical image MI is received, the volumetric medical image MI comprising at least one organ 309 or a portion thereof. Further, in step 301 of FIG. 9, an atlas A is provided as an example of above-mentioned certain reference coordinate system A, L. The atlas A has a plurality of coordinates, wherein the atlas A includes a single reference volume of the at least one organ 309 or the portion thereof.

In step 302 of FIG. 9, the certain input I is provided. According to step 302 of FIG. 9, the certain input I of FIG. 9 includes a first sparse sampling descriptor D1 associated with the certain point of interest 310 in the volumetric medical image MI and a second sparse sampling descriptor D2 associated with a certain target location TL in the atlas A.

In step 303, a conditional regression model RM for estimating anatomical locations is applied to the present certain input I including said first sparse sampling descriptor D1 and said second sparse sampling descriptor D2. The conditional regression model RM outputs a relative displacement vector Δx, Δy, Δz referring to the atlas A.

The foregoing examples have been provided merely for the purpose of explanation and are in no way to be construed as limiting of the present framework disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein, rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A computer-implemented method for automated processing of volumetric medical images, the method comprising:

a) receiving a volumetric medical image, wherein the volumetric medical image comprises at least one organ or portion thereof; and b) outputting a normalized location or a relative location referring to a certain reference coordinate system by applying a regression model for estimating anatomical locations to a certain input, wherein the certain input comprises a sparse sampling descriptor associated with a certain point of interest in the volumetric medical image, wherein the sparse sampling descriptor comprises a vector of intensities of sampled voxels associated with the certain point of interest, wherein the regression model comprises a neural network trained to embody a normalized coordinate estimator for point matching between locations in the volumetric medical image and locations in the certain reference coordinate system, wherein the neural network outputs coordinates of the normalized location between 0 and 1.

2. The method of claim 1, wherein the regression model comprises a residual network.

3. The method of claim 1, further comprising:

receiving a command for determining the certain point of interest.

4. The method of claim 3, wherein the sparse sampling descriptor is provided in dependence on the command.

5. The method of claim 1, further comprising:

providing a sparse sampling model for sparse sampling the volumetric medical image; and sampling voxels from the volumetric medical image using the provided sparse sampling model for obtaining sparse sampling descriptors.

6. The method of claim 5, wherein the sparse sampling model defines a number N of sampling points distributed in the volumetric medical image and defining locations and distances of the distributed sampling points.

7. The method of claim 1, wherein the certain reference coordinate system comprises an atlas having a plurality of coordinates, said atlas including a single reference volume of the at least one organ or the portion thereof.

8. The method of claim 7, wherein, in the atlas, at least one coordinate of the plurality of coordinates of the atlas is associated with associated knowledge.

9. The method of claim 8, wherein the associated knowledge comprises semantic anatomical information.

10. The method of claim 7, wherein outputting the normalized location or the relative location referring to the certain reference coordinate system comprises outputting a normalized location referring to the atlas.

11. The method of claim 10, further comprising:

mapping the certain point of interest of the volumetric medical image to a certain normalized location of the atlas and associating knowledge at or near that certain normalized location from the atlas.

12. The method of claim 1, wherein the certain reference coordinate system uses at least a certain landmark in the volumetric medical image, wherein outputting the normalized location or the relative location referring to the certain reference coordinate system comprises outputting a relative location referring to the certain landmark.

13. The method of claim 12, wherein, for a certain location, the sparse sampling descriptor associated with the certain location is provided and a displacement from the certain landmark is determined.

14. The method of claim 1, wherein outputting the normalized location or the relative location referring to the certain reference coordinate system comprises outputting a relative displacement vector relative to an atlas.

15. The method of claim 1, further comprising:

storing findings in the volumetric medical image using the normalized location or the relative location, and determining, based on the normalized location or the relative location, information associated with the certain point of interest or associated with at least a location nearby the certain point of interest.

16. The method of claim 15, further comprising:

executing image registration based on the normalized location or the relative location.

17. The method of claim 16 wherein executing the image registration comprises matching the certain point of interest to a location in a further image.

18. A device for automated processing of volumetric medical images, comprising:

one or more processing circuits; and a non-transitory memory coupled to the one or more processing circuits, the non-transitory memory comprising a module configured to perform steps including a) receiving a volumetric medical image, wherein the volumetric medical image comprises at least one organ or portion thereof, and b) outputting a normalized location or a relative location referring to a certain reference coordinate system by applying a regression model for estimating anatomical locations to a certain input, wherein the certain input comprises a sparse sampling descriptor associated with a certain point of interest in the volumetric medical image, wherein the sparse sampling descriptor comprises a vector of intensities of sampled voxels associated with the certain point of interest, wherein the regression model comprises a neural network trained to embody a normalized coordinate estimator for point matching between locations in the volumetric medical image and locations in the certain reference coordinate system, wherein the neural network outputs coordinates of the normalized location between 0 and 1.

19. The device of claim 18 wherein the regression model comprises a residual network.

20. One or more non-transitory computer-readable media comprising machine readable instructions, that when executed by one or more processing units, cause the one or more processing units to perform method steps comprising:

a) receiving a volumetric medical image, wherein the volumetric medical image comprises at least one organ or portion thereof; and b) outputting a normalized location or a relative location referring to a certain reference coordinate system by applying a regression model for estimating anatomical locations to a certain input, wherein the certain input comprises a sparse sampling descriptor associated with a certain point of interest, wherein the sparse sampling descriptor comprises a vector of intensities of sampled voxels associated with the certain point of interest, wherein the regression model comprises a neural network trained to embody a normalized coordinate estimator for point matching between locations in the volumetric medical image and locations in the certain reference coordinate system, wherein the neural network outputs coordinates of the normalized location between 0 and 1.

* * * * *